United States Patent
Garcia De Lomas Durante (10) Patent No.: US 12,072,326 B2
(45) Date of Patent: Aug. 27, 2024

(54) THERMAL IMAGE ANALYSER FOR CROPS

(71) Applicant: LOMASGROW HOLDING B.V., Wageningen (NL)

(72) Inventor: Javier Garcia De Lomas Durante, Wageningen (NL)

(73) Assignee: LOMASGROW HOLDING B.V., Bennekom (NL)

( * ) Notice: Subject to any disclaimer, the term of this patent is extended or adjusted under 35 U.S.C. 154(b) by 345 days.

(21) Appl. No.: 17/599,038

(22) PCT Filed: Apr. 3, 2020

(86) PCT No.: PCT/NL2020/050227
§ 371 (c)(1),
(2) Date: Sep. 28, 2021

(87) PCT Pub. No.: WO2020/204716
PCT Pub. Date: Oct. 8, 2020

(65) Prior Publication Data
US 2022/0178898 A1    Jun. 9, 2022

(30) Foreign Application Priority Data
Apr. 3, 2019   (NL) .................................... 1043218

(51) Int. Cl.
*G01N 33/00* (2006.01)
*A01G 7/04* (2006.01)
(Continued)

(52) U.S. Cl.
CPC ......... *G01N 33/0098* (2013.01); *A01G 7/045* (2013.01); *G01J 5/085* (2013.01);
(Continued)

(58) Field of Classification Search
CPC .... G01N 33/0098; G01N 21/84; G01N 21/01; G01N 2021/0112; G01N 2021/8466;
(Continued)

(56) References Cited

U.S. PATENT DOCUMENTS 5,023,459 A    6/1991   Osborn
2019/0377946 A1*  12/2019   Genty .................... G06V 10/82

OTHER PUBLICATIONS

O. M. Grant et al: "Thermal imaging to detect spatial and temporal variation in the water status of grapevine ( *Vitis vinifera* L.)", Journal of Horticultural Science and Biotechnology, vol. 91, No. 1, Jan. 2, 2016 (Jan. 2, 2016), pp. 43-54, XP055710177, GB ISSN: 1462-0316, (Year: 2016).*

(Continued)

*Primary Examiner* — Brandon J Miller
(74) *Attorney, Agent, or Firm* — BROWDY AND NEIMARK, P.L.L.C.

(57) ABSTRACT

The present invention provides a thermal image analyser for the analysis of the stomatal conductance s of a plant, which comprises a thermal imaging device, configured to capture a thermal image of at least a portion of the plant that is in an imaging region of the thermal imaging device, and a processor device, configured to analyse the captured thermal image and to determine the stomatal conductance of the plant on the basis of the captured thermal image. The thermal image analyser further comprises a reference object, which comprises a reference surface and a thermal sensor, wherein the thermal sensor is connected to the reference surface and configured to emit a sensor signal that is representative for a surface temperature of the reference surface. The reference object is adapted to be positioned, such that at least a portion of the reference surface is located in the imaging region of the thermal imaging device. The sensor signal is adapted to be transmitted to the processor device, and the processor device is configured to compen- (Continued)

sate the stomatal conductance on the basis of the captured thermal image and the sensor signal.

19 Claims, 4 Drawing Sheets

(51) Int. Cl.
  *G01J 5/00* (2022.01)
  *G01J 5/08* (2022.01)
  *G01K 1/14* (2021.01)
  *G01K 7/02* (2021.01)
  *H05B 47/105* (2020.01)

(52) U.S. Cl.
  CPC .............. *G01K 1/14* (2013.01); *G01K 7/02* (2013.01); *H05B 47/105* (2020.01); *G01J 2005/0077* (2013.01)

(58) Field of Classification Search
  CPC .. A01G 7/045; G01J 5/085; G01J 2005/0077; G01J 5/53; G01K 7/02; G01K 1/14; H05B 47/105
  See application file for complete search history.

(56) References Cited

OTHER PUBLICATIONS

Mangus Devin L et al: "Development and evaluation of thermal infrared imaging system for high spatial and temporal resolution crop water stress monitoring of corn within a greenhouse", Computers and Electronics in Agriculture, Elsevier, Amsterdam, NL, pp. 149-v159, vol. 121, (Dec. 2015).

Azar Khorsandi et al: "Plant temperature-based indices using infrared thermography for detecting water status in sesame under greenhouse conditions", Agricultural Water Management, vol. 204, pp. 222-233, (Apr. 2018).

H. G. Jones, "Use of infrared thermography for monitoring stomatal closure in the field: application to grapevine", Journal of Experimental Botany, vol. 53, No. 378, pp. 2249-226 (Nov. 2002).

Jones Hamlyn G et al., "A practical method using a network of fixed infrared sensors for estimating crop canopy conductance and evaporation rate", Biosystems Engineering, Academic Press, UK, vol. 165, pp. 1537-5510 (Oct. 2017).

Ermanno Grinzato: "Humidity and air temperature measurement by quantitative infrared thermography", QIRT Journal—Quantitative Infrared Thermography: An International Journal on IR Thermography, pp. 55-72 vol. 7, No. 1, (Jun. 2010).

Anonymous: "Holstein Flowers first Thermoview user—Warmtebeeldcamera.nl", ((May 20218) XP055651513, URL: <https://www.warmtebeeldcamera.nl/nl/bl ogs/nieuws/holstein-flowers-first-thermovi ew-user[gevonden>.

Pou Alicia et al: "Validation of thermal iindices for water status identification in grapevine", Agricultural Water Management, Elsevier, Amsterdam, NL, pp. 60-72, vol. 134, (Dec. 2013).

Maes Wouter H et al: "A new wet reference target method for continuous infrared thermography of vegetations", Agricultural and Forest Meteorology, Elsevier, Amsterdam, NL, pp. 119-131, vol. 226, (Jul. 2016).

O. M. Grant et al: 11 Thermal imaging to detect spatial and temporal variation in the water status of grapevine ( *Vi tisinifera* L. Journal of Horticultural Science and Biotechnology, pp. 43-54 vol. 91, No. 1. (Jan. 2016).

* cited by examiner

THERMAL IMAGE ANALYSER FOR CROPS

TECHNICAL FIELD

The present invention relates to a thermal image analyser for the analysis of a stomata status, e.g. the stomatal conductance of a plant. The present invention further relates to a reference object for use in a thermal image analyser, to a method for the analysis of a stomata status, e.g. the stomatal conductance of a plant and to a method for calibration of a reference object for a thermal image analyser.

BACKGROUND ART

In botany, stomata are pores, found in the epidermis of leaves, stems, and other organs, that facilitate gas exchange, e.g. $CO_2$ ingress and water transpiration. The pores are bordered by a pair of specialized parenchyma cells known as guard cells that are responsible for regulating the size of the stomatal opening. The stomatal opening can vary from fully open to completely closed and is critical for optimum operation. Stomata react in minutes to climatic conditions and play a crucial role in photosynthesis. Generally, a fully opened stomatal opening is desired by growers, since that may provide for the largest possible growing speed of the plants.

Greenhouses are typically adapted to create optimal climatic conditions for the crops that are grown inside the greenhouses. Methods have therefore been developed to analyse the stomata, for instance to determine the conditions whereby the stomata open and close, e.g. the stomata status. From prior art, it is known from that plant temperature in combination with climate data can be used for stomata status analysis. Stomata status information can thereby be used to optimize conditions for plants.

Known thermal image analysers for the determination of stomata status rely on one or more remote thermal cameras, which are able to determine the surface temperature of the plants from a distance, without physically contacting the plants, in order to determine the stomata status. However, these known thermal image analysing devices are relatively inaccurate, due to inconsistencies between the actual plant temperatures and measured values thereof in captured thermal images. The result of this inaccurateness may be that the stomata status of the plant is estimated wrongly and that the watering of the plants and/or the light radiation towards the plants may either be too low and/or too high to ensure optimal growth of the plants.

In KR20180058293 and US2018238740, which both do not relate to the determination of stomata status of plants, methods are disclosed, which are configured to reduce such inconsistencies between temperature measurements. According to these methods, remote non-contact temperature sensors are provided, which are configured to locally measure a temperature of an imaged object, after which the captured thermal images are corrected on the basis of the temperature that is measured with the remote non-contact temperature sensor.

In Mangus et. al. (2016), a device is known that is configured to monitor water stress of plants. Water stress may influence the stomatal conductance of plants, but is not representative therefore only by itself, since stomatal conductance may only be governed by light radiation, temperature and relative air humidity. Hence, on the basis of water stress alone, it is not possible to determine stomata status information of plants, such as the stomatal conductance of the plants.

In Khorsandi et. al. (2018), a device is disclosed that is configured to determine stomatal conductance of plants, and a relationship between watering of plants and their stomatal conductance is given.

In Jones et. al. (2018), a method of establish crop canopy conductance is disclosed. Although crop canopy conductance appears to be similar to stomatal conductance, are the measurement techniques from this prior art document not applicable for determining stomatal conductance, in particular not for nurseries or the like, in which only small plants are present. The know measurements techniques only enables global determination of conductance, e.g. of the entire crop canopy, but does not enable local measurements for individual plants.

However, these known correction methods do not provide for sufficient reduction of the inconsistencies. In particular for the determination of the stomata status of plant, an accuracy of less than approximately 1° C. may be required, because temperature differences between the air and the plants, e.g. leaves, may also be under 1° C. This may especially be the case for the typical high air humidity environments that are present in greenhouses.

It is therefore an object of the invention to provide a thermal image analyser that is configured to more accurately determine the stomata status of crops, or at least to provide an alternative thermal image analyser.

SUMMARY OF INVENTION

The present invention provides a thermal image analyser for the analysis of a stomata status, e.g. the stomatal conductance of a plant, comprising:

a thermal imaging device, configured to capture a thermal image of at least a portion of the plant that is in an imaging region of the thermal imaging device, and a processor device, configured to analyse the captured thermal image and to determine stomata status information, e.g. the stomatal conductance of the plant on the basis of the captured thermal image, characterized in that the thermal image analyser further comprises:

a reference object, which comprises a reference surface and a thermal sensor, wherein the thermal sensor is connected to the reference surface and configured to emit a temperature sensor signal that is representative for a surface temperature of the reference surface, wherein the reference object is adapted to be positioned, such that at least a portion of the reference surface is located in the imaging region of the thermal imaging device, wherein the temperature sensor signal is adapted to be transmitted to the processor device, and wherein the processor device is configured to compensate the determined stomata status information e.g. the stomatal conductance on the basis of the captured thermal image and the temperature sensor signal.

The thermal image analyser according to present invention comprises a thermal imaging device, which is configured to capture thermal images of the plant. At least portions of the plants that are in an imaging region of the thermal imaging device are imaged, after which the corresponding thermal image may comprise thermal information of the imaged portions of the plants, e.g. comprising information about surface temperatures of these portions of the plants.

In an embodiment, the thermal imaging device may be provided as a thermal camera, which is configured to capture thermal images that may have a two-dimensional size of multiple pixel, preferably a two-dimensional size that is sufficiently large to visually display the thermal image to a user. An example of such a thermal camera is an uncooled bolometer camera, which may have a two-dimensional sensor having a few hundred by a few hundred pixels.

The thermal imaging device according to the present invention enables the obtained thermal images to be two-dimensional images. This allows the establishing of a two-dimensional temperature profile, instead of only a one-dimensional (averaged) point measurement, as is for example done with a conventional infrared thermometer or pyrometer for measuring temperatures.

The temperature profile enables the temperature, and thus also the stomatal conductance, to be established in more detail. In particular when used in nurseries, having very small plants surrounded by soil, one cannot assure himself that a point measurement gives an accurate representation of the temperatures. Hence, such a temperature average may be largely influenced by the temperature of the soil that is erroneously measured, instead of only by the plants. With the two-dimensional temperature profile, the temperature is displayed in more detail and the temperatures of the plants may be extracted from the entire temperature profile, in order to result in an accurate determination of the stomatal conductance.

The processor device is configured to analyse the thermal images and is configured to deduct stomata status information e.g. the stomatal conductance from the surface temperatures of the plant, as comprised in the thermal images. The processor device may in particular be configured to export stomata status information or may even be configured to control a climate installation, in order to change the climate in the environment of the plant, or to control a lighting system, to change the illumination of the plant, in order to bring the deducted the stomatal conductance of the plant towards a desired the stomatal conductance that is optimal for the growth of the plant.

According to the present invention, the thermal image analyser comprises a reference object, which is configured to be suspended adjacent the plant, such the reference object is located in the imaging region of the thermal imaging device and that the reference object may be visible in the thermal images that are to be captured by the thermal imaging device.

The reference object comprises a reference surface, which is configured to be directed towards the thermal imaging device, such that at least a portion of the reference surface is visible in the thermal images that are to be captured by the thermal imaging device.

The reference object further comprises a thermal sensor, which is connected to the reference surface. The thermal sensor may be positioned on a side of the reference surface that faces away from the thermal imaging device, or may at least be provided on a portion of the reference surface that is not in the imaging region, and therefore not visible in the thermal images that are to be captured. As such, the temperature sensor may be prevented from disadvantageously influencing the temperature information in the thermal image that is to be captured from the reference surface.

The thermal sensor is configured to measure a surface temperature of the reference surface, and preferably configured to measure a temperature of a side of the reference surface that faces towards the thermal imaging device, or may at least be configured to measure the temperature of a portion of the reference surface that is in the imaging region of the thermal imaging device, such that the measured temperature corresponds to that of a portion of the reference surface that is visible in the thermal images that are to be captured.

The thermal sensor is configured to provide a temperature sensor signal that is representative for the measured surface temperature of the reference surface. This temperature sensor signal is adapted to be transmitted to the processor device.

The processor device is, in turn, configured to compensate the determined stomata status information, e.g. the stomatal conductance on the basis of the captured thermal image and the temperature sensor signal. Hence, the measured temperatures in the thermal image may not accurately correspond to the actual temperatures of the plant of which the thermal image is captured. However, the reference surface of the reference object is, with the analyser according to the present invention, also displayed in the thermal image. The surface temperature of the reference surface may be accurately measured by the thermal sensor of the reference object, which means that at least the actual temperature of the reference surface in the thermal image is accurate. Accordingly, the reference surface in the thermal image may function as a reference for the determination of the stomatal conductance of the plant.

Upon comparing, with the processor device, the measured surface temperature of the reference surface, as provided in the transmitted temperature sensor signal, with its temperature displayed in the thermal image, the difference between both temperatures may be determined by the processor device. Knowing this temperature difference, the processor device may be configured to incorporate this temperature difference in the stomatal conductance and may, accordingly, correct the e.g. the stomatal conductance for errors in the thermal image, e.g. differences between the measured temperatures of the plant in the thermal image and the actual surface temperatures of the plant.

Furthermore, the reference object in the imaging region of the thermal imaging device acts as a dry leaf reference surface. Normally, as is for example disclosed in Mangus et. al. (2016), such a dry leaf temperature can only be established by guessing on the basis of the measured actual leaf temperature. A generally used estimation is that the dry leaf temperature is 5° C. above the actual leaf temperature. However, such an estimation is rather inaccurate.

With the reference object in the present thermal image analyser, it is no longer necessary to estimate the dry leaf temperature on the basis of the actual temperature of the leaves, but it can rather be measured using the reference object. Accordingly, the stomatal conductance can be determined accurately with the thermal image analyser according to the present invention.

The thermal image analyser according to the present invention provides, with respect to the known devices, the advantage that more accurate measurements may be taken of the surface temperatures of the plant, and therefore more accurate information on the stomata status, e.g. the stomatal conductance of the plant may be established. The invention may further provide that a distribution of stomata status over the entire plant may be established, rather than solely in certain locations of the plant. Additionally, as is described above, the distribution enables distinguishing between the measured temperatures, for temperatures corresponding to plants and for temperatures of other surrounding objects, such as the soil. Moreover, the present invention may provide for a thermal image analyser for plants that is relatively inexpensive, in comparison to the known devices, yet still more accurate than the known devices.

As a result of the accurate determination of the stomata status, e.g. the stomatal conductance of the plants, the conditions of the environment of the plants may be tuned to be optimal in order to ensure the highest possible growing speed and/or best quality of the product. On the basis of this more accurate stomatal conductance, the watering of the plants may be tuned to avoid spillage of the water and/or to prevent the plants from drowning in excess water. Alternatively or additionally, the amount of provided light may be tuned to prevent wasting electrical by producing excess light and/or to prevent the plants from drying out under excess light.

In an embodiment of the thermal image analyser, a surface characteristic of the reference surface substantially corresponds to a surface characteristic of leaves of the plant. By providing these corresponding surface characteristics, the reference surface more accurately mimics leaves of the plant, which may provide that, during use of the thermal image analyser, differences in between the surface temperature of the reference surface of the reference object and the leaves of the plant are further reduced. Additionally, the reference surface may have an artificial stomatal conductance that may correspond to a dry leaf stomatal conductance of the plant.

In a further embodiment, the surface characteristic may be the shape of the reference surface of the reference object, which may correspond to the shape of the leaves of the plant. As such, the aerodynamic and/or thermodynamic behaviour of the reference surface may correspond more accurately to the aerodynamic and/or thermodynamic behaviour of the leaves of the plant, which may provide the result that heat convection occurring between the reference surface and its environment may accurately correspond to the heat convection that occurs between the leaf of the plant and the environment thereof.

In an additional or alternative embodiment, the surface characteristic of the reference surface is the colour thereof. The reference surface may, according to this embodiment, have a colour of which the emissivity substantially corresponds to the emissivity of surfaces of the leaves of the plant. As such, the heat radiation that is, at least during use of the thermal image analyser, emitted by the plant substantially corresponds to the heat radiation that is emitted by the reference surface of the reference object, such that the reference surface even more accurately mimics leaves of the plant and that the surface temperatures of both may correspond.

In a further embodiment, the colour of the reference surface is a grey colour in the visible regime, e.g. having a wavelength in between 400 nm and 800 nm. Alternatively, the colour of the reference surface may as well have other wavelength and may be in other regimes, such as the infrared regime.

In an embodiment, the reference object comprises a cap, which is formed by a spheroid wall and the reference surface is formed by a spherical outer surface of the spheroid wall. Preferably, the spheroid wall of the cap forms a half-sphere, wherein the outer surface of the half-sphere, e.g. a convex outer surface, forms the reference surface of the reference object and faces at least partially towards the thermal imaging device. The opposing inner surface of the half-sphere, e.g. a concave inner surface, faces at least partially away from the thermal imaging device. The spheroid wall may provide the advantage that a boundary layer may be created adjacent the inner surface, which may correspond to a boundary layer that is present underneath a leaf of a plant, such that the aerodynamic and/or thermodynamic behaviour of the cap more accurately corresponds to the aerodynamic and/or thermodynamic behaviour of the leaf of the plant.

Alternative to a spheroid wall, the cap may as well have a different shape, preferably defining an interior at a side of the cap that faces away from the thermal imaging device.

In a further embodiment, the temperature sensor is a thermocouple on an inner surface of the spheroid wall. Preferably, when the spherical wall forms a half-sphere, the concave inner surface of the spherical wall defines the interior of the cap and faces towards the interior. The thermocouple may be located against the inner surface of the spherical wall at a central portion of the half-sphere. As such, the thermocouple is in physical contact with the dry leaf reference object, and is thus able to measure the temperature of the reference object in more detail, when compared to the remote infrared thermometers or pyrometers that are known from the prior art.

In an alternative or additional embodiment, the cap of the reference object has a diameter in the range between 20 mm and 100 mm, for example being 40 mm. This range for the diameter has, in practise, been found by the applicant to be small enough to allow simultaneous imaging of the reference surface and the plant, but has also been found to be sufficiently large to allow the reference surface to be actually visible in the thermal images that are to be captured by the thermal imaging device.

In an alternative or additional embodiment, the spheroid wall of the cap has a thickness in the range between 0.1 mm and 2 mm. This range for the thickness has, in practise, been found by the applicant to be small enough to prevent shielding of the thermal sensor and to allow for sufficient transmission of heat from the reference surface of the reference object towards the temperature sensor, but has also been found to be sufficiently large to prevent the cap from becoming too delicate to handle and from being carried away by possible ventilation streams in the environment of the thermal image analyser and the plant.

In an embodiment, the reference object comprises a plastic material. The reference object may for example comprise a celluloid plastic. The provision of a plastic material for the reference object, and in particular the use thereof for the reference surface, provides that surface characteristics of the reference surface, such as the emissivity of heat radiation, accurately corresponds to that of leaves of the plant.

In an embodiment, the thermal image further comprises a transmitter device, which is configured to transmit the temperature sensor signal from the thermal sensor towards the processor device. The transmitter device provides that the thermal sensor may be located remote from the processor device, since it is able to transmit the temperature sensor signal over a distance. The transmitter device may comprise a wired connection for electrically connecting the thermal sensor and the processor device.

Alternatively or additionally, the transmitter device may also comprise a wireless communication device, e.g. comprising a sending device and a receiving device, for the wireless transmitting of the temperature sensor signal. This wireless transmission may be in particular advantageous, since it does not require a physical connection between the thermal sensor and the processor device. As such, the reference object and/or the processor device with the thermal imaging device may be movable along multiple plants. The wireless transmitting may even allow a single processor device to communicate with a plurality of thermal sensors of different reference objects, without requiring any physical connection between them.

In an embodiment, the processor device comprises a memory with micro climate data of an environment of the plant at least temporarily stored thereon. The micro climate data comprises one or more of:

an air temperature of the environment, and/or a relative air humidity of the environment.

The micro climate data may thereby represent other measured values that represent the conditions of the environment in which the plants are located. In particular, the micro climate data may represent measured values of the conditions in a greenhouse in which the plants are located.

According to this embodiment, the processor device is, on the basis of the stomata status, e.g. the stomatal conductance and the micro climate data, configured to determine one or more of:

a dew point status distribution of the plant, a maximum allowable air temperature decrease for which condensation on the plant is prevented, a maximum allowable increase in air humidity for which condensation on the plant is prevented, and a maximum allowable decrease in surface temperature of the plant for which condensation on the plant is prevented.

The dew point of the plant may generally be a function of temperature and air humidity. In particular, the temperature of the plant, air temperature of the environment and air humidity of the environment are relevant for the dew point. Below the dew point, condensation of moisture may occur on the plant, which may, e.g. depending on the growth status of the plant, be advantageous or disadvantageous for the growth of the plant. Hence, the condensation may result in the growth of fungus, which is disadvantageous for the growth of the plants.

According to this embodiment, the processor device may, given a situation where there is no condensation on the plant, be able to determine a maximum allowable drop in the air temperature of the environment. When the temperature drop remains smaller than this maximum allowable drop, no condensation will occur on the plant. When the temperature drop is larger than this maximum allowable drop, condensation will occur on the plant. Similarly, the processor device may be configured to calculate the maximum possible increase in air humidity of the environment to prevent or to allow condensation on the plant and may be configured to calculate the maximum possible decrease in surface temperature of the plant to prevent or to allow condensation on the plant.

In an embodiment, the thermal image analyser further comprises a light sensor. The light sensor may be adapted to be located in the proximity of the plant and is configured to emit a light sensor signal that is representative for light conditions in the proximity of the plant. The light sensor may be in particular configured to measure the amount of radiation that is present in the environment of the plant, for example comprising daylight and/or artificial light, such that the processor device may be configured to determine the behaviour of the reference object and/or the leaves of the plant under the influence of the light.

In an embodiment, the thermal image analyser further comprises an air temperature sensor. The air temperature sensor may be adapted to be located in the environment of the plant and is configured to emit an air temperature sensor signal that is representative for the air temperature of the environment. The air temperature sensor may be connected with the processor device, in order to provide a storage of the processor device with updated data on the air temperature of the environment of the plant.

In an embodiment, the thermal image analyser further comprises a air humidity sensor. The air humidity sensor may be adapted to be located in the environment of the plant and is configured to emit an air humidity sensor signal that is representative for the relative air humidity of the environment. The air humidity sensor may be connected with the processor device, in order to provide a storage of the processor device with updated data on the relative air humidity in the environment of the plant. This may be advantageous, since the stomatal conductance of plants is not dependent on the temperature of their leaves alone, but also on the relative air humidity of the plants.

In a further embodiment, the thermal image analyser is configured to compensate the determined stomatal conductance on the basis of the air humidity sensor signal, in order to also take the air humidity into account when determining the stomatal conductance.

In an embodiment, the thermal image analyser further comprises a CO2-sensor. The CO2-sensor may be adapted to be located in the environment of the plant and is configured to emit a CO2 sensor signal that is representative for the CO2-content of the air in the environment. The measured CO2-content may be fed towards the processor device, which may, on the basis of the measured CO2-content, be configured to compare the stomata status, e.g. the stomatal conductance of the plant with the amount of CO2 in the environment. On the basis of the comparison, the processor device may be configured to determine whether the CO2-content is optimal for the stomata status, e.g. the stomatal conductance, or vice versa, and may be configured to control the CO2-content of the environment, in order to be optimal for the stomata status, e.g. the stomatal conductance of the plant.

In an embodiment, the thermal image analyser further comprises a substrate sensor, which is adapted to be associated with a substrate of the plant, e.g. adapted be at least partially inserted in the substrate. The substrate sensor is configured to emit a substrate sensor signal that is representative for a parameter of the substrate. The substrate parameter may be one or more of a volumetric water content, an electrical conductivity and/or a substrate temperature.

The substrate sensor signal may be fed towards the processor device and may the basis for the calculation of the stomata status data, e.g. the stomatal conductance and/or for the controlling of properties of the substrate. For example, the watering of the plants may be adjusted on the basis of the determined stomatal conductance.

The present invention further provides a reference object for use in a thermal image analyser, comprising a reference surface, which is configured to be imaged by a thermal imaging device of the thermal image analyser, and a thermal sensor, which is connected to the reference surface and configured to emit a temperature sensor signal that is representative for a surface temperature of the reference surface. The reference object is adapted to be positioned adjacent a plant of which a stomata status, e.g. the stomatal conductance is to be analysed by the thermal image analyser and the temperature sensor signal is adapted to be used by a processor device of the thermal image analyser as a basis for compensating the determined stomatal conductance.

According to the present invention, the reference object may be suspended adjacent the plant, such the reference object is located in an imaging region of a thermal imaging device and that the reference object may be visible in thermal images that are to be captured by the thermal imaging device. The reference object, and in particular the reference surface thereof, is configured to be directed towards the thermal imaging device, such that at least a portion of the reference surface may be visible in the thermal images that are to be captured by the thermal imaging device.

The thermal sensor of the reference object is connected to the reference surface. The thermal sensor may be positioned on a side of the reference surface that is adapted to face away from the thermal imaging device, or may at least be provided on a portion of the reference surface that is adapted to not be in the imaging region of the thermal imaging device, and therefore not visible in the thermal images that are to be captured.

The thermal sensor is configured to measure a surface temperature of the reference surface. Preferably, the thermal sensor may at least be configured to measure the temperature of a portion of the reference surface that is adapted to be in the imaging region of the thermal imaging device, such that the measured temperature corresponds to that of a portion of the reference surface that may be visible in the thermal images that are to be captured.

The thermal sensor is configured to provide a temperature sensor signal that is representative for the measured surface temperature of the reference surface. This temperature sensor signal is adapted to be transmitted to a processor device of the thermal image analyser.

The thermal sensor may be a thermocouple on an inner surface of a spheroid wall of the reference object. Preferably, when the spherical wall forms a half-sphere, the concave inner surface of the spherical wall defines the interior of the reference object. The thermocouple may be located against the inner surface of the spherical wall at a central portion of the half-sphere. As such, the thermocouple is in physical contact with the dry leaf reference object, and is thus able to measure the temperature of the reference object in more detail, when compared to the remote infrared thermometers or pyrometers that are known from the prior art.

The present invention further provides a lighting system for illuminating plants in a cultivation system, comprising:
the thermal image analyser that is described above,
a control unit, which is connected to the thermal image analyser, and
an illumination source, which is connected to the control unit and configured to emit light for illuminating plants,
wherein the thermal image analyser is configured to transmit the compensated stomatal conductance to the control unit, and wherein the control unit is configured to compare the compensated stomatal conductance with a predefined optimal stomatal conductance for the plants and configured to control the illumination source on the basis of the comparison.

In the lighting system according to the present invention, the control unit is configured to control the illuminating of the plants in dependence of the determined stomatal conductance. The lighting system further comprises an illumination source, which may, for example, be embodied as a Light Emitting Diode (LED), configured to emit light at various different wavelengths and/or at various different intensities.

Light radiation is one of the factors that determines the stomatal conductance of the plant, which implies that the stomatal conductance of the plant can be optimized by adjusting the illumination, e.g. the light radiation that is emitted towards the plants.

The control unit is configured to compare the determined stomatal conductance with a predefined optimal stomatal conductance, wherein this optimal stomatal conductance may be the largest possible stomatal conductance for that specific type of plant, in order to obtain the largest conduction of water vapour and carbon dioxide through the pores of the plant's leaves, e.g. between the plant and its microclimate, e.g. the direct surroundings.

At this optimal stomatal conductance, the circumstances for the plants are optimal, resulting in the best possible growth conditions for the plant. The control unit is configured to control the illumination source, in order to adjust the illumination towards the plants. By changing the illumination conditions, the growth circumstances for the plants may be improved, resulting in an increased yield.

As a result of the improved growth conditions, the stomatal conductance of the plants may change towards the predefined optimal stomatal conductance. This change can be observed by the control unit, which is, in turn, configured to further control the illumination source for keeping the growth conditions, e.g. the light radiation at this optimal level.

In an embodiment of the lighting system, the control unit is configured to control the illumination source by controlling one or more of:
activation of the illumination source to emit light for illuminating the plants,
deactivation of the illumination source to cancel illumination of the plants when a certain predefined illumination duration has lapsed,
the intensity of the light that is emitted by the illumination source, and/or
the spectrum of the light that is emitted by the illumination source.

By controlling one or more of these variables, the lighting conditions for the plants may be improved. With the activation or deactivation of the illumination source, the duration for which the plant are subjected to the light can be set. It is a general rule amongst growers that the plants should be subjected to light as long as possible. This rule may either be confirmed by the lighting system according to the present invention, or one may find out that the stomatal conductance of the plants remains the best when the plants are not subjected to the light radiation the whole time.

The intensity of the emitted light may be adjusted, in order to prevent the light from being either too bright or too dark, in order to ensure optimal growth of the plants. With a high intensity of the emitted light, in particular at the onset of emitting light towards the plants, the initial stomatal conductance will be high, but will drop soon afterwards at a relatively high rate. With a too low light intensity, the stomatal conductance may not be very high, but may remain substantially constant over time and will only drop at a lower rate. It is desirable to find an optimum in between, resulting in a stomatal conductance that is as high as possible and also constant for the largest possible time.

Similarly, the spectrum of the emitted light may be adjusted, in order to ensure that the colour of the emitted light is optimal, giving the best possible growth of the plants.

In an embodiment of the lighting system, the control unit is configured to compare the compensated stomatal conductance with a predefined optimal stomatal conductance in a mathematical stomatal conductance model.

This implies that the control unit is configured to input the compensated stomatal conductance in a mathematical model of the plant as a starting point value. Then, the control unit is, in the mathematical model, configured to model changes to a growth variable for the plant. For example, the control unit may set a certain value for the spectrum and/or intensity of light that is emitted towards the plant in the mathematical model. On the basis of this set value, the stomatal conductance of the plant in the mathematical model may change. The control unit is, in turn, configured to compare the changed stomatal conductance with the starting point value. When the stomatal conductance of the plant in the mathematical model were to increase, the set growth variable apparently has a positive effect on the stomatal conductance of the plant in the mathematical model.

The control unit is configured to note that the setting of that respective variable will have a positive effect on the stomatal conductance of the actual plant as well. Accordingly, the control unit may control the illumination source to be changed towards a similar growth variable as well.

In case the modelled growth variable reduces the stomatal conductance of the plant in the mathematical model, the control unit is configured to set a different growth variable in the mathematical model, in order to find out whether such a change would result in an increased stomatal conductance.

The present invention further provides a method for the analysis of a stomata status, e.g. the stomatal conductance of a plant. The method comprises the steps of:
  positioning a thermal imaging device, such that at least a portion of the plant is in an imaging region of the thermal imaging device,
  positioning a reference object, such that at least a portion of the reference surface of the reference object is located in the imaging region of the thermal imaging device,
  capturing, with the thermal imaging device, a thermal image of the plant and the reference surface in the imaging region,
  obtaining, with a thermal sensor of the reference object, a temperature sensor signal that is representative for a surface temperature of the reference surface,
  determining, with a processor device, stomata status information, e.g. the stomatal conductance of the plant, wherein the stomata status information is determined on the basis of the captured thermal image, and
  compensating, with the processor device, the determined stomata status information, e.g. the stomatal conductance of the plant, wherein the stomata status information is compensated on the basis of the captured thermal image and the temperature sensor signal.

The method according to the present invention may be carried out by means of a thermal image analyser according to the present invention and/or by means of a reference object according to the present invention. Thereto, the method may comprise the step of providing a thermal image analyser according to the present invention and/or the step of providing a reference object according to the present invention.

First, the method comprises the step of the positioning of a thermal imaging device, such that the plant is at least partially in an imaging region of the thermal imaging device. The location of the imaging region corresponds to the thermal image that is captured by the thermal imaging device, which implies that the portion of the plant that is in the imaging region, is also visible in the thermal image that is to be captured by the thermal imaging device. This positioning of the thermal imaging device may take place repetitively, in order reposition the thermal imaging device each time after a thermal image has been captured. As such, a single thermal imaging device may be used to capture thermal images of multiple portions of a plant and/or of multiple plants.

The method further comprises the step of the positioning of the reference object, which is at least partially positioned in the imaging region of the thermal imaging device, or at least in a region where the imaging region of the thermal imaging device will be located after the positioning of the thermal imaging device. As such, the reference object, and in particular the reference surface thereof, will be visible in the thermal images that are to be captured by the thermal imaging device.

The positioning of the reference object may take place repetitively in order to allow for the compensation in multiple thermal images, taken at multiple locations. This variant may be convenient when the thermal image analyser comprises a single reference object. Alternatively, in particular when the thermal image analyser comprises multiple reference objects, the positioning may comprise the positioning of the multiple reference objects, which may be configured to remain in place after positioning, without being repositioned afterwards.

The step of capturing may take place after the thermal imaging device and the reference object have been positioned, such that the captured thermal image comprises thermal information of at least a portion of the plant and that the reference object is visible in the thermal image as well, such that the thermal image also comprises thermal information of at least a portion of the reference surface of the reference object.

For each of the captured thermal images, a temperature sensor signal may be provided that is representative for the surface temperature of the reference surface. Preferably, the temperature sensor signal is obtained simultaneously with the capturing of the thermal image, such that both the measured temperature of the reference surface and the thermal image are both established at substantially the same moment and that both correspond to each other over time. The obtained temperature sensor signal may be transmitted to the processor device, for example by means of a wireless transmitting device.

The processor device is, first of all, configured to determine stomata status information, e.g the stomatal conductance on the basis of the thermal image. The stomata status of a plant may be determined on the basis of its temperature, and in particular of a surface temperature of leaves of the plant. The processor device may comprise a memory, in which stomata status information, e.g. the stomatal conductance of various plants may be stored, in relation to surface temperatures. The processor device may be configured to analyse the imaged temperature profile of the plant, which is visible in the captured thermal image, and may be configured to determine corresponding stomata status information, e.g. the stomatal conductance on the basis of the temperature profile.

The stomata status information, as determined by the processor device, is entirely based on the imaged temperature profile in the captured thermal image. It was found by the applicant that the imaged temperature profile does not always accurately correspond to the actual surface temperatures of the imaged portions of the plant. The method according to the present invention thereto further comprises the step of compensating the determined stomata status information, e.g. the stomatal conductance.

The compensating of the stomata status information, e.g. of the stomatal conductance is carried out by the processor device and is done on the basis of the temperature sensor signal that is obtained by the thermal sensor of the reference object and on the basis of the captured thermal image. In the thermal image, the reference surface of the reference object is displayed, which implies that the thermal image also comprises thermal information about the reference surface, which may, as mentioned above, not necessarily correspond to the actual surface temperature of the reference surface. The temperature of the reference object is representative for the dry leaf temperature of the leaves of the plants. Since the reference object is visible in the thermal images, the dry leaf temperature is visible in the thermal image, and may serve the purpose of being an absolute reference for the temperature profile that is visible in the thermal image.

The surface temperature of the reference surface has, on the other hand, been accurately measured by the thermal sensor of the reference object. This means that, despite the non-accurate temperature information in the thermal image, at least the actual temperature of the reference surface in the temperature sensor signal may be substantially accurate. Hence, the dry leas temperature of the reference object does not need to be established out of the thermal image, but can rather be measured in absolute manner by the thermal sensor, e.g. the thermocouple thereof.

The processor device may be configured to compare the measured surface temperature of the reference surface, as provided in the transmitted temperature sensor signal, with the temperature of the reference surface, e.g. a dry leaf temperature that is displayed in the thermal image. In particular, the difference, e.g. the error between both temperatures may be determined by the processor device. Knowing this temperature difference, the processor device may be configured to incorporate this temperature difference in the determined stomata status information, e.g. the stomatal conductance and may, accordingly, correct the determined stomata status information, e.g. the stomatal conductance for errors in the thermal image.

For example, the dry leaf reference surface may provide for an absolute temperature value in determining differences between the measured surface temperatures of the plant in the thermal image and the actual surface temperatures of the plant.

Finally, the compensated stomata status information, e.g. the stomatal conductance of the plant may be exported to be analysed by an operator. Alternatively or additionally, the compensated stomata status information, e.g. the stomatal conductance may be fed towards a climate controller, which may be configured to control the climate in the environment of the plant, or to control a lighting system, to change the illumination of the plant, in order to improve the environment and to promote the growth of the plant on the basis of the compensated stomata status information, e.g. the stomatal conductance.

The method according to the present invention provides, with respect to the known methods, the advantage that more accurate thermal information may be established about the temperatures of the plant, therefore resulting in more accurate information on the stomata status, e.g. the stomatal conductance of the plant. The invention further provides that a distribution of stomata status, e.g. the stomatal conductance over the entire plant may be established, rather than solely in certain locations of the plant. Moreover, the present invention may provide for a method that can be carried out relatively inexpensive, in comparison to the known methods, yet still more accurate than the known methods.

In an embodiment, the method further comprises the step of determining, with the processor device and on the basis of the stomata status, e.g. the stomatal conductance and micro climate data of an environment of the plant, one or more of:

a dew point status distribution of the plant, a maximum allowable air temperature decrease for which condensation on the plant is prevented, a maximum allowable increase in air humidity for which condensation on the plant is prevented, and a maximum allowable decrease in surface temperature of the plant for which condensation on the plant is prevented, The micro climate data of the environment of the plant is at least temporarily stored on a memory of the processor device and comprises one or more of:

an air temperature of the environment, and/or a relative air humidity of the environment.

The dew point of the plant may generally be a function of temperature and air humidity. In particular, the temperature of the plant, air temperature of the environment and air humidity of the environment are relevant for the dew point. Below the dew point, condensation of moisture may occur on the plant, which may, e.g. depending on the growth status of the plant, be advantageous or disadvantageous for the growth of the plant.

According to this embodiment of the method, the processor device may, given a situation where there is no condensation on the plant, determine a maximum allowable drop in the air temperature of the environment. When the temperature drop remains smaller than this maximum allowable drop, no condensation will occur on the plant. When the temperature drop is larger than this maximum allowable drop, condensation will occur on the plant Similarly, the processor device may calculate the maximum possible increase in air humidity of the environment to prevent or to allow condensation on the plant and may be configured to calculate the maximum possible decrease in surface temperature of the plant to prevent or to allow condensation on the plant.

According to this embodiment, the compensated stomata status information, e.g. the stomatal conductance may be fed towards a climate controller, which may be configured to control the climate in the environment of the plant, or to control a lighting system, to change the illumination of the plant, in order to promote the growth of the plant on the basis of the compensated stomata status information. Accordingly, the climate controller may be adapted to transmit micro climate data towards the processor device, in particular during the controlling of the climate in the environment of the plant, in order to provide the processor device with up-to-date micro climate information, which may contribute to the accurate determination of the stomata status, e.g. of the stomatal conductance of the plant.

The present invention further provides a method for controlling the micro-climate of plants, comprising the steps of:

the method for the analysis of a stomata status, e.g. the stomatal conductance of a plant as described above, transmitting the compensated stomatal conductance to a control unit of a lighting system, comparing, with the control unit, the compensated stomatal conductance with a predefined optimal stomatal conductance for the plants, and controlling, with the control unit, an illumination source of the lighting system on the basis of the comparison.

With the controlling method according to the present invention, the control unit is controls the illuminating of the plants in dependence of the determined stomatal conductance, in order to control the micro-climate of the plants. The illumination source that is used may, for example, be embodied as a Light Emitting Diode (LED), configured to emit light at various different wavelengths and/or at various different intensities.

The micro-climate is defined as being the climate for the plant at minimal distance from the plants, for example being the climate of a boundary layer surrounding the plants. The exchange of carbon dioxide and water vapour takes place at this boundary layer, which forms the interface between the plant and the surroundings of the plant. By controlling the micro-climate in this boundary layer, the growth conditions for the plant may be improved, which would result in an increased stomatal conductance.

Light radiation is one of the factors that determines the stomatal conductance of the plant, which implies that the stomatal conductance of the plant can be optimized by adjusting the illumination, e.g. the light radiation that is emitted towards the plants.

According to the method, the control unit is used to compare the determined stomatal conductance with a predefined optimal stomatal conductance, wherein this optimal stomatal conductance may be the largest possible stomatal conductance for that specific type of plant, in order to obtain the largest conduction of water vapour and carbon dioxide through the pores of the plant's leaves, e.g. between the plant and its micro-climate, e.g. the direct surroundings.

At this optimal stomatal conductance, the circumstances for the plants are optimal, resulting in the best possible growth conditions for the plant. The control unit controls the illumination source, in order to adjust the illumination towards the plants. By changing the illumination conditions, the growth circumstances for the plants may be improved, resulting in an increased yield.

As a result of the improved growth conditions, the stomatal conductance of the plants may change towards the predefined optimal stomatal conductance. This change can be observed by the control unit, which is, in turn, configured to further control the illumination source for keeping the growth conditions, e.g. the light radiation at this optimal level.

In an embodiment of the method, the controlling of the illumination source is the controlling of one or more of:

activation of the illumination source to emit light for illuminating the plants, deactivation of the illumination source to cancel illumination of the plants when a certain predefined illumination duration has lapsed, the intensity of the light that is emitted by the illumination source, and/or the spectrum of the light that is emitted by the illumination source.

By controlling one or more of these variables, the lighting conditions for the plants may be improved. With the activation or deactivation of the illumination source, the duration for which the plant are subjected to the light can be set. It is a general rule amongst growers that the plants should be subjected to light as long as possible. This rule may either be confirmed by the lighting system according to the present invention, or one may find out that the stomatal conductance of the plants remains the best when the plants are not subjected to the light radiation the whole time.

The intensity of the emitted light may be adjusted, in order to prevent the light from being either too bright or too dark, in order to ensure optimal growth of the plants. With a high intensity of the emitted light, in particular at the onset of emitting light towards the plants, the initial stomatal conductance will be high, but will drop soon afterwards at a relatively high rate. With a too low light intensity, the stomatal conductance may not be very high, but may remain substantially constant over time and will only drop at a lower rate. It is desirable to find an optimum in between, resulting in a stomatal conductance that is as high as possible and also constant for the largest possible time.

Similarly, the spectrum of the emitted light may be adjusted, in order to ensure that the colour of the emitted light is optimal, giving the best possible growth of the plants.

In an embodiment of the controlling, the comparing by the control unit is done on the basis of a mathematical stomatal conductance model.

This implies that the control unit is configured to input the compensated stomatal conductance in a mathematical model of the plant as a starting point value. Then, the control unit is, in the mathematical model, configured to model changes to a growth variable for the plant. For example, the control unit may set a certain value for the spectrum and/or intensity of light that is emitted towards the plant in the mathematical model. On the basis of this set value, the stomatal conductance of the plant in the mathematical model may change. The control unit is, in turn, configured to compare the changed stomatal conductance with the starting point value. When the stomatal conductance of the plant in the mathematical model were to increase, the set growth variable apparently has a positive effect on the stomatal conductance of the plant in the mathematical model.

The control unit is configured to note that the setting of that respective variable will have a positive effect on the stomatal conductance of the actual plant as well. Accordingly, the control unit may control the illumination source to be changed towards a similar growth variable as well.

In case the modelled growth variable reduces the stomatal conductance of the plant in the mathematical model, the control unit is configured to set a different growth variable in the mathematical model, in order to find out whether such a change would result in an increased stomatal conductance.

The present invention furthermore provides a method for calibration of a thermal image analyser. The calibration method comprises the steps of:

positioning a reference object of the thermal image analyser adjacent a plant, emitting, by a thermal sensor of the reference object, a temperature sensor signal that is representative for a surface temperature of a reference surface of the reference object, measuring a temperature of the plant, comparing the temperature sensor signal and the measured temperature of the plant, and setting, in a processor device of the thermal image analyser, a correction factor for the temperature sensor signal, in order to compensate for differences between the temperature sensor signal and the measured temperature of the plant.

The method for the calibration of the reference object may provide that the temperature sensor signal, as emitted by the thermal sensor of the reference object, accurately corresponds to the actual surface temperature of the plant. By calibrating the reference object, the compensating of the stomata status information, e.g. the stomatal conductance, as carried out by the processor device, may become more accurate, resulting in an improved analysis of the stomata status, e.g. the stomatal conductance of the plant.

For the calibration of the reference object, first, the reference object is positioned at a location near the plant. This may provide that the environmental conditions for the reference surface, e.g. air temperature and air humidity, are substantially the same as for the plant itself. Then, the temperature of the reference surface is measured with the thermal sensor and the corresponding temperature sensor signal is emitted by the thermal sensor. Preferably simultaneously, the surface temperature of the plant is measured. This measuring preferably takes place with a calibrated contact thermometer, in order to provide for an accurate measured temperature. A comparison is then made between the measured surface temperature of the plant and the temperature of the reference surface, which is comprised in the temperature sensor signal. The comparison between both may thereby form a measure for a possible deviation between the surface temperature of the plant and the temperature of the reference surface of the reference object.

Finally, a correction factor may be set in a processor device of the thermal image analyser. The correction factor may be based on the deviation between the surface temperature of the plant and the temperature of the reference surface of the reference object, as followed from the above-mentioned comparison. The correction factor in the processor device may, during use of the thermal image analyser for the analysis of the stomata status, e.g. the stomatal conductance of the plant, be used to correct the transmitted temperature sensor signal, which was representative for the measured temperature of the reference surface of the reference object, to more accurately correspond to the actual surface temperature of the plant.

BRIEF DESCRIPTION OF THE DRAWINGS

Further characteristics of the invention will be explained below, with reference to embodiments, which are displayed in the appended drawings, in which.

Throughout the figures, the same reference numerals are used to refer to corresponding components or to components that have a corresponding function.

DESCRIPTION OF EMBODIMENTS

Figure 1:
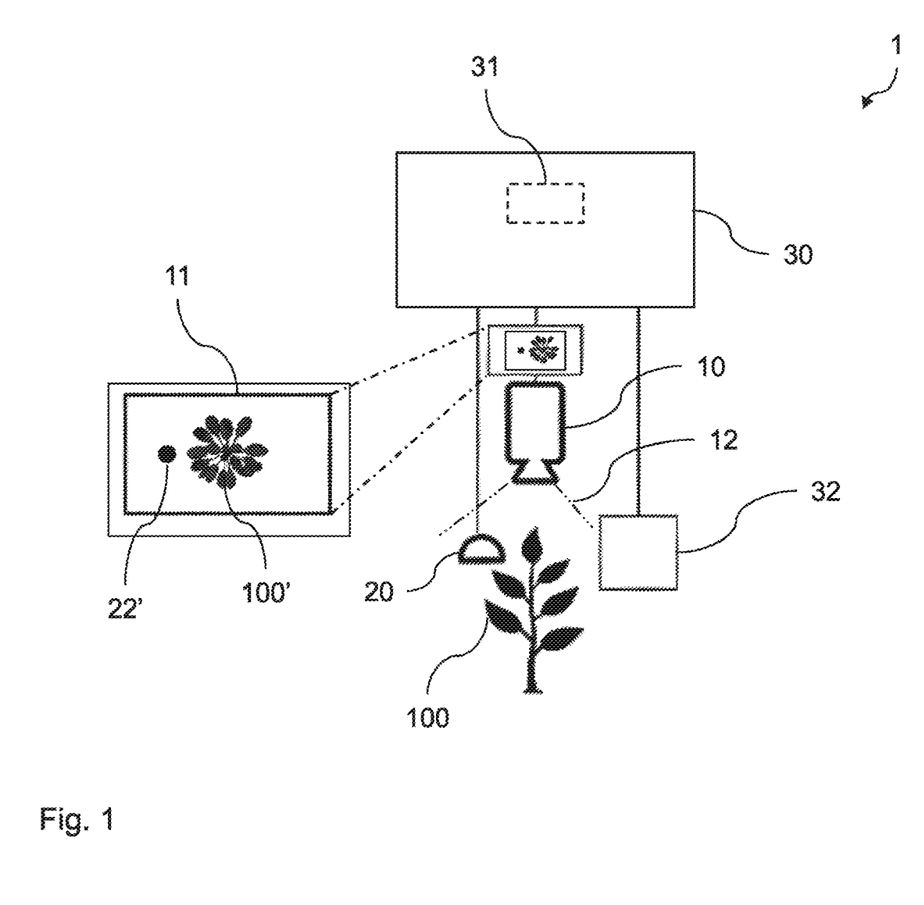
FIG. 1 schematically depicts an embodiment of the thermal image analyser according to the present invention, FIG. 2 schematically depicts an embodiment of the reference object according to the present invention, FIG. 3a schematically depicts a thermal image of a plant and a reference object, FIG. 3b schematically depicts stomata status information, e.g. the stomatal conductance of the plant, as may be obtained by the method according to the present invention, and FIG. 4 schematically depicts an embodiment of the lighting system according to the present invention.

FIG. 1 schematically an embodiment of the thermal image analyser according to the present invention, to which is referred with reference numeral 1. The analyser 1 is configured to analyse stomata status information, e.g. the stomatal conductance of a plant 100. The analyser 1 comprises a thermal imaging device, which is provided as a thermal camera 10. The thermal camera 10 is configured to capture a thermal image 11 of at least a portion of the plant 100 that is located in an imaging region 12 of the thermal camera 10.

The analyser 1 furthermore comprises a reference object 20, which is provided as an artificial leaf. The reference object 20 is suspended next to the plant 100. As such, at least a reference surface 22 of the reference object 20 is located in the imaging region 12 of the thermal camera 10. The reference object 22 is therefore also visible in the thermal image 11 that is captured by the thermal camera 10.

The analyser 1 further comprises a processor device 30, which is electrically connected to the thermal camera 10 and to the reference object 20, e.g. by means of a transmitter device, which is provided as a wire 21. Alternatively, the processor device may as well be wirelessly connected to the thermal camera and/or to the reference object.

The processor device 30 is configured to receive the thermal image 11 from the thermal camera 10 and is configured to analyse the thermal image 11. Upon analysing the thermal image 11, the processor device 30 is configured to determine stomata status information, e.g. the stomatal conductance of the plant 100, which follows from the temperature information 100' of the plant 100 that is incorporated in the thermal image 11.

The processor device 30 is furthermore configured to receive a temperature sensor signal from a thermal sensor 23 of the reference object 20. The temperature sensor signal is representative for a surface temperature of the reference surface 22, and in particular of the portion of the reference surface 22 that is located in the imaging region 12 of the thermal camera 10.

The temperature information 100' of the plant 100 in the thermal image 11 may not accurately correspond to the actual temperature of the plant 100, due to possible inaccurateness of the thermal camera 10. To compensate for this incorrectness, the processor device 30 is configured to compensate the stomata status information, e.g. the stomatal conductance on the basis of the captured thermal image 11 and the temperature sensor signal.

The processor device 30 may thereto be configured to recognise the reference surface 22 of the reference object 20 in the thermal image 11 and may be able to compare the corresponding temperature information 22' of the reference surface 22, as incorporated in the thermal image 11, with the measured temperature of the reference surface 22, as incorporated in the temperature sensor signal that is emitted by the thermal sensor 23.

The processor device 30 comprises a memory 31 with micro climate data of an environment of the plant 100 at least temporarily stored thereon. The micro climate data comprises an air temperature of the environment of the plant 100, and a relative air humidity of the environment. The processor device 30 may further comprise a sensor device 32 to measure the micro climate data, e.g. the air temperature and relative air humidity, in the proximity of the plant 100, in order to provide the processor device 30 with up-to-date micro climate information to for the determining of the stomata status, e.g. the stomatal conductance of the plant 100.

The processor device 30 is, on the basis of the stomata status, e.g. the stomatal conductance and the micro climate data, configured to determine a dew point status distribution of the plant 100, e.g. the distribution, over the plant 100, of the plant surface temperature and/or air temperature below which condensation would occur on the plant 100. The processor device 30 may be further configured to determine a maximum allowable air temperature decrease, or a maximum allowable decrease in surface temperature of the plant 100, for which condensation on the plant 100 is prevented. Furthermore, the processor device 30 may be configured to determine a maximum allowable increase in air humidity for which condensation on the plant 100 is prevented.

Figure 2:
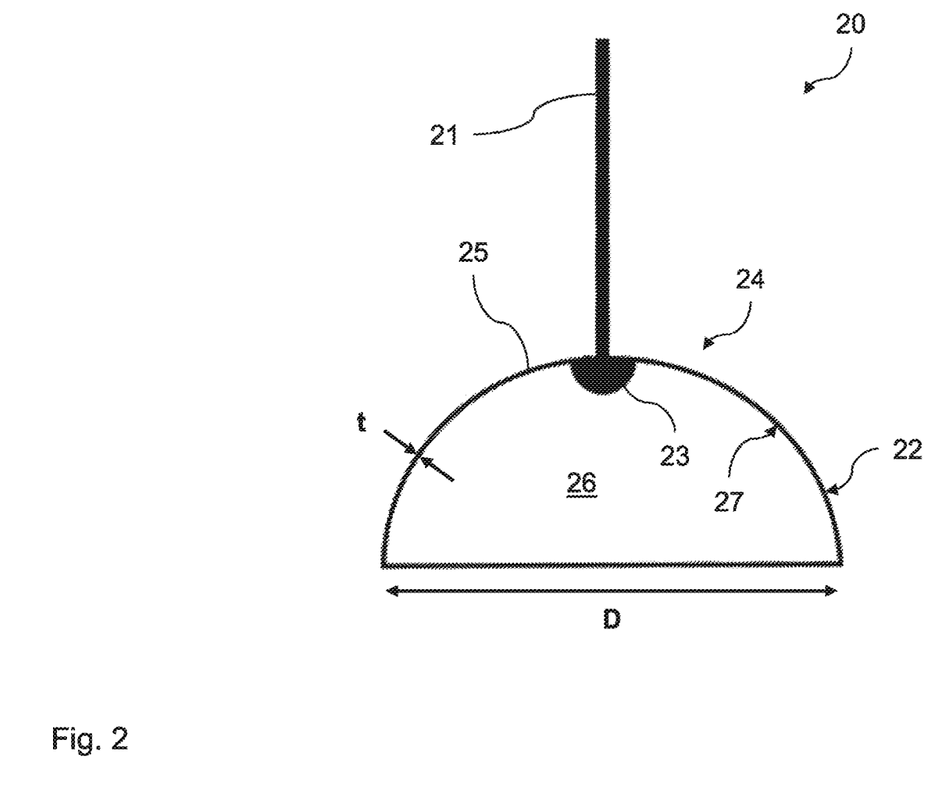

In FIG. 2, an embodiment of the reference object 20 is displayed in more detail. The reference object 20 comprises a cap 24, which is defined by spheroid wall 25, which forms a half-sphere. The cap 24 is suspended from a wire 21 and may hang next to a plant. The wire 21 is configured to form a transmitter device between the reference object 20 and a processor device of a thermal image analyser.

The spheroid wall 25 of the cap 24 defines an interior 26 of the cap 24. An inner concave surface 27 of the spheroid wall 25 thereby faces towards the interior 26 of the cap 24, whereas a convex outer surface of the spheroid wall 25 forms the reference surface 22 of the reference object 20. This reference surface 22 of the reference object 20 is adapted to face the thermal imaging device and is adapted to be located in an imaging region of the thermal imaging device, in order to be visible in the thermal image that is to be captured.

The thermal sensor 23 is located in the interior 26 of the cap 24 and is connected to the spheroid wall 25, in order to provide that the measured temperature by the thermal sensor 23 accurately corresponds to the surface temperature of the reference surface 22, without requiring the thermal sensor to be actually arranged on the reference surface, which could disadvantageously influence the temperature information in the thermal image that is to be captured from the reference surface 22.

The reference surface 22 of the reference object 20, e.g. the convex outer surface of the spheroid wall 25 has a surface characteristic that substantially corresponds to a surface characteristic of leaves of the plant 100. Moreover, the reference surface 22 has a colour of which the emissivity substantially corresponds to the emissivity of surfaces of the leaves of the plant 100. As such, the heat radiation that is, at least during use of the thermal image analyser, emitted by the plant 100 substantially corresponds to the heat radiation that is emitted by the reference surface 22 of the reference object 20, such that the reference surface 22 more accurately mimics leaves of the plant 100.

The cap 24 of the reference object 20 has a diameter (D), which is in the range between 20 mm and 100 mm. In the embodiment that is displayed in FIG. 2, the diameter (D) of the cap 24 is approximately 40 mm.

The spheroid wall 25 of the cap 24 of the reference object has a thickness (t), which is in the range between 0.1 mm and 2 mm. In the embodiment that is displayed in FIG. 2, the thickness (t) of the spheroid wall 25 of the cap 24 is approximately 0.5 mm.

The reference object 20 comprises a plastic material. In particular, the spheroid wall (25) of the cap (24) of the reference object comprises a celluloid plastic, of which a surface characteristic has been found to accurately correspond to a surface characteristic of the plant 100, in order to provide that the reference surface 22 forms an accurate representation of leaves of the plant 100. Moreover, the reference surface may have a grey colour in the visible regime, which was found to have a radiation emissivity that substantially corresponds to the radiation emissivity of leaves of a plant.

Figure 3A:
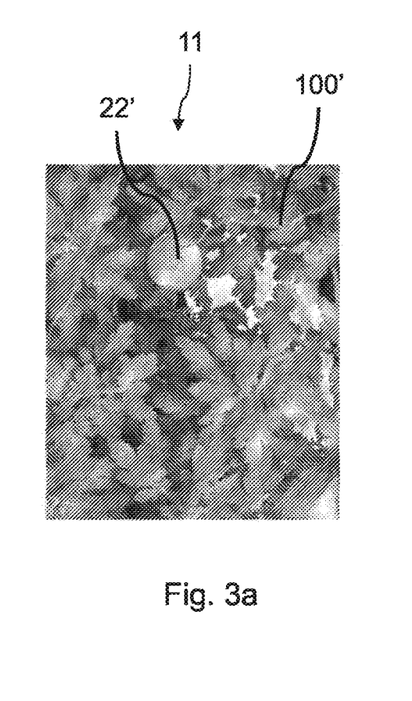

FIG. 3a schematically depicts a thermal image 11 in which a plant and a reference object are visible. This thermal image 11 has been captured by thermal imaging device of a thermal image analyser according to the present invention. In the thermal image 11, a thermal representation of the plant, referred to with reference numeral 100', and a thermal representation of the reference surface of the reference object, referred to with reference numeral 22', are displayed.

Figure 3B:
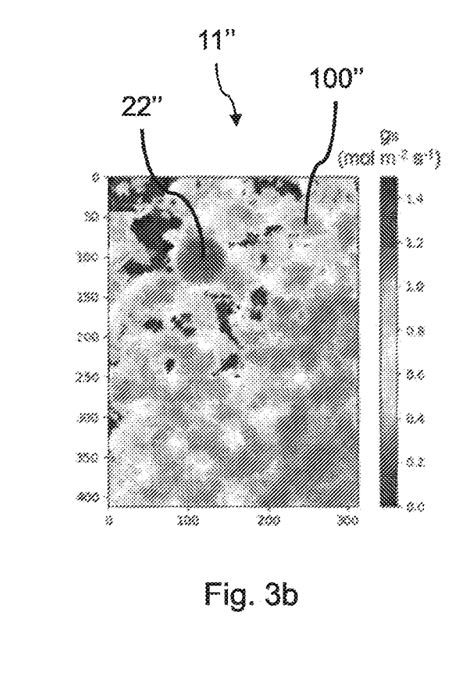

The processor device of the thermal image analyser according to the present invention is configured to analyse the thermal image 11 and configured to determine stomata status information, e.g. the stomatal conductance on the basis of the thermal image 11. FIG. 3b schematically depicts the stomata status information, e.g. the stomatal conductance of the plant, of which the graphical representation is referred to with reference numeral 11". The stomata status information, e.g. the stomatal conductance is provided as a coloured contour map 11", having a scale for the stomatal conductance ($g_s$) in the range between 0.0 mol m$^{-2}$ and 1.5 mol m$^{-2}$ s$^{-1}$. The lower limit is, in the contour map 11", represented by a red colour and the upper limit is represented by a blue colour.

In the contour map 11", the stomatal conductance of the plant, referred to with reference numeral 100", and the stomatal conductance of the reference surface of the reference object, referred to with reference numeral 22", are both displayed.

The surface temperature of the reference surface 22 of the reference object 20 is known from the temperature sensor signal that is transmitted by the thermal sensor 23 of the reference object 20. Since the reference surface 22 accurately mimics the leaves of the plant 100, the processor device 30 may correct the temperature information in the thermal image 11 on the basis of the temperature sensor signal with the actual temperature of the reference surface 22. Accordingly, the processor device 30 may be able to compensate the stomata status information, e.g. the stomatal conductance on the basis of the thermal image 11 and the actual temperature of the reference surface 22.

Figure 4:
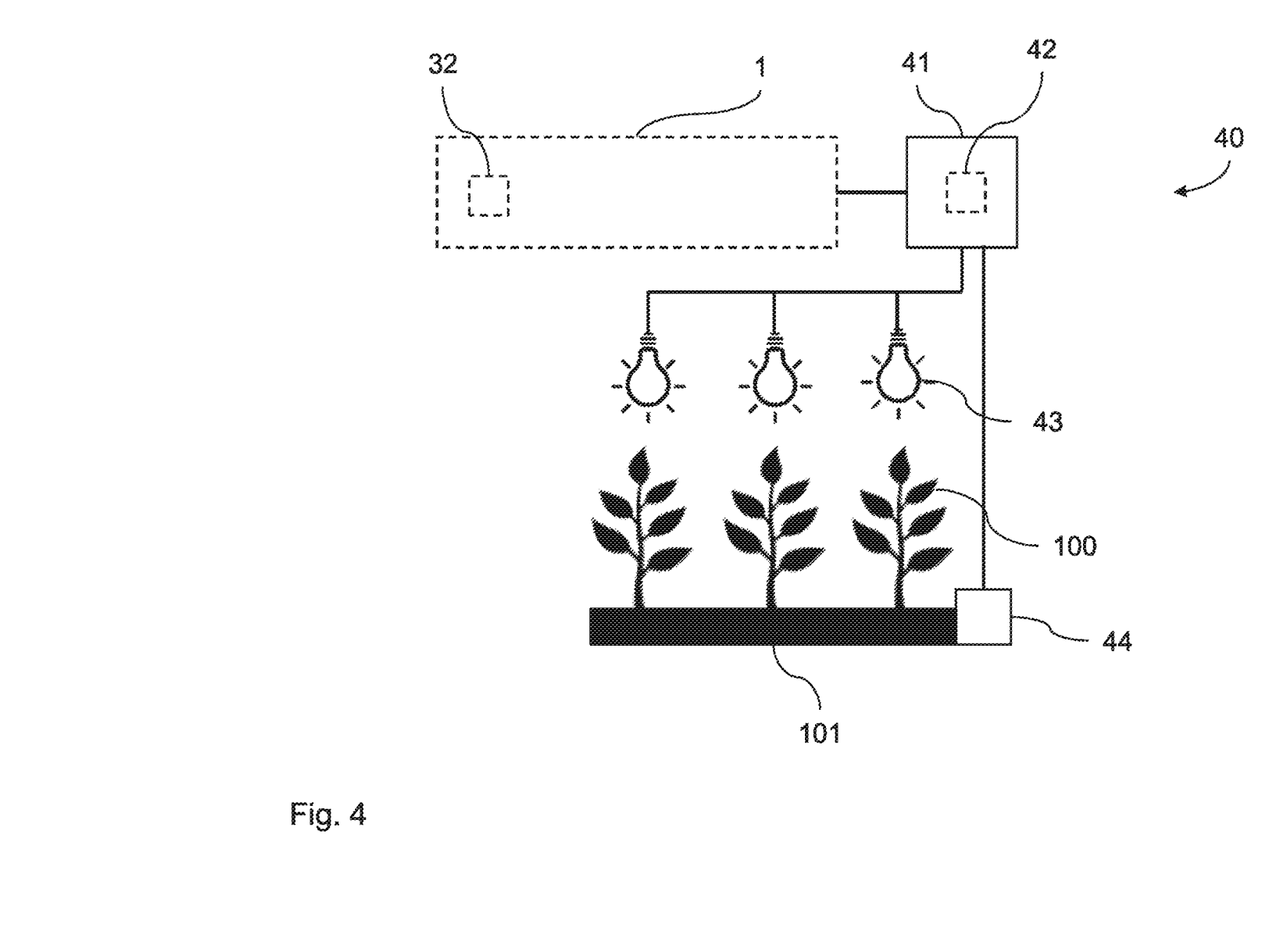

FIG. 4 schematically an embodiment of the lighting system according to the present invention, to which is referred with reference numeral 40. The lighting system 40 comprises a thermal image analyser 1 that is similar to the embodiment described above. This thermal image analyser 1 is configured to analyse the stomatal conductance of plants 100 that are planted in soil 101.

The lighting system 40 comprises a control unit 41, which is connected to the thermal image analyser 1. The thermal image analyser 1 is configured to transmit the compensated stomatal conductance to the control unit 41, after which the control unit 41 is configured to compare the compensated stomatal conductance with a predefined optimal stomatal conductance for the plants 100.

The lighting system 40 further comprises an illumination source 43, which is configured to emit light at various different wavelengths and/or at various different intensities, in order to illuminate the plants 100. The control unit 41 is configured to control the illumination source 43 on the basis of the comparison between the compensated stomatal conductance and the predefined optimal stomatal conductance.

The control unit 41 is configured to compare the determined stomatal conductance with a predefined optimal stomatal conductance in a mathematical stomatal conductance model 42 that is stored in the control unit 41. This optimal stomatal conductance may be the largest possible stomatal conductance for that specific type of plant 100, in order to obtain the largest conduction of water vapour and carbon dioxide through the pores of the plant's leaves, e.g. between the plant 100 and its micro-climate, e.g. the direct surroundings.

The control unit 41 is configured to input the compensated stomatal conductance in the mathematical model 42 of the plant as a starting point value. Then, the control unit 41 is, in the mathematical model 42, configured to model changes to a growth variable for the plant. For example, the control unit 41 may set a certain value for the spectrum and/or intensity of light that is emitted towards the plant in the mathematical model 42. On the basis of this set value, the stomatal conductance of the plant in the mathematical model 42 may change. The control unit 41 is, in turn, configured to compare the changed stomatal conductance with the starting point value. When the stomatal conductance of the plant in the mathematical model 42 were to increase, the set growth variable apparently has a positive effect on the stomatal conductance of the plant in the mathematical model 42.

The control unit 41 is configured to note that the setting of that respective variable will have a positive effect on the stomatal conductance of the actual plant 100 as well.

Accordingly, the control unit 41 may control the illumination source 43 to be changed towards a similar growth variable as well.

In case the modelled growth variable reduces the stomatal conductance of the plant in the mathematical model 42, the control unit 41 is configured to set a different growth variable in the mathematical model 42, in order to find out whether such a change would result in an increased stomatal conductance.

The control unit 41 of the lighting system 40 is configured to control the illumination source 43 by controlling activation and deactivation of the illumination source 43 to emit light for illuminating the plants 100 for a certain predefined illumination duration. Furthermore, the control unit 41 may control the illumination source 43 to change the intensity and/or the spectrum of the light that is emitted by the illumination source 43.

The control unit 41 is further configured to control the illumination source 43 on the basis of a micro-climate sensor signal from a sensor device 32 in the thermal image analyser 1. This sensor device 32 is configured to measure air temperature and relative air humidity, in the proximity of the plant 100, in order to enable accurate determining of the stomatal conductance of the plant 100 by the thermal image analyser 1.

Similarly, the illumination system 40 comprises a soil sensor 44, which is configured to measure parameters of the soil 101, such as moisture content and soil temperature. The soil sensor 44 is connected to the control unit 41 and the control unit 44 is configured to control the illumination source 43 on the basis of soil sensor signal as well.

The invention claimed is:

1. A thermal image analyser for determining the stomatal conductance of a plant, comprising:
    a thermal imaging device, configured to capture a thermal image of at least a portion of the plant that is in an imaging region of the thermal imaging device, and
    a processor device, configured to analyse the captured thermal image and to determine the stomatal conductance of the plant on the basis of the captured thermal image,
    wherein the thermal image analyser further comprises:
    a reference object, which comprises a reference surface and a thermal sensor, wherein the thermal sensor is connected to the reference surface and configured to emit a temperature sensor signal that is representative for a surface temperature of the reference surface,
    wherein the reference object further comprises a cap, which is formed by a spheroid wall and wherein the reference surface is formed by a spherical outer surface of the spheroid wall,
    wherein the reference object is adapted to be positioned, such that at least a portion of the reference surface is located in the imaging region of the thermal imaging device,
    wherein the temperature sensor signal is adapted to be transmitted to the processor device, and
    wherein the processor device is configured to compensate the stomatal conductance on the basis of the portion of the plant and the reference surface in the imaging region of the thermal imaging device shown in the captured thermal image and the temperature sensor signal.

2. The thermal image analyser according to claim 1, wherein a surface characteristic of the reference surface substantially corresponds to a surface characteristic of leaves of the plant.

3. The thermal image analyser according to claim 2, wherein the reference surface has a colour of which the emissivity substantially corresponds to the emissivity of surfaces of the leaves of the plant.

4. The thermal image analyser according to claim 1, wherein the temperature sensor is a thermocouple on an inner surface of the spheroid wall.

5. The thermal image analyser according to claim 1, wherein the cap has a diameter in the range between 20 mm and 100 mm and/or wherein the spheroid wall of the cap has a thickness in the range between 1 mm and 2 mm.

6. The thermal image analyser according to claim 1, wherein the reference object comprises a plastic material, preferably comprising a celluloid plastic.

7. The thermal image analyser according to claim 1, further comprising an air humidity sensor, which is connected to the processor device and configured to emit an air humidity sensor signal that is representative for the relative air humidity of the environment.

8. The thermal image analyser according to claim 7, wherein the processor device is further configured to compensate the stomatal conductance on the basis of the air humidity sensor signal.

9. The thermal image analyser according to claim 1, further comprising a transmitter device, which is configured to transmit the sensor signal from the thermal sensor towards the processor device.

10. The thermal image analyser according to claim 1, wherein the processor device comprises a memory with micro climate data of an environment of the plant at least temporarily stored thereon,
    wherein the micro climate data comprises one or more of:
        an air temperature of the environment, and
        a relative air humidity of the environment, and
    wherein the processor device is, on the basis of the stomatal conductance and the micro climate data, configured to determine one or more of:
        a dew point status distribution of the plant,
        a maximum allowable air temperature decrease for which condensation on the plant is prevented,
        a maximum allowable increase in air humidity for which condensation on the plant is prevented, and
        a maximum allowable decrease in surface temperature of the plant for which condensation on the plant is prevented.

11. The method for calibration of a thermal image analyser according to claim 10, comprising the steps of:
    positioning a reference object of the thermal image analyser adjacent a plant,
    emitting, by a thermal sensor of the reference object, a sensor signal that is representative for a surface temperature of a reference surface of the reference object,
    measuring a temperature of the plant,
    comparing the sensor signal and the measured temperature of the plant, and
    setting, in a processor device of the thermal image analyser, a correction factor for the sensor signal, in order to compensate for differences between the sensor signal and the measured temperature of the plant.

12. A lighting system for illuminating plants in a cultivation system, comprising:
    the thermal image analyser according to claim 1,
    a control unit, which is connected to the thermal image analyser, and
    an illumination source, which is connected to the control unit and configured to emit light for illuminating plants, wherein the thermal image analyser is configured to transmit the compensated stomatal conductance to the control unit, and wherein the control unit is configured to compare the compensated stomatal conductance with a predefined optimal stomatal conductance for the plants and configured to control the illumination source on the basis of the comparison.

13. The lighting system according to claim 12, wherein the control unit is configured to control the illumination source by controlling one or more of:

activation of the illumination source to emit light for illuminating the plants, deactivation of the illumination source to cancel illumination of the plants when a certain predefined illumination duration has lapsed, the intensity of the light that is emitted by the illumination source, and/or the spectrum of the light that is emitted by the illumination source.

14. The lighting system according to claim 12, wherein the control unit is configured to compare the compensated stomatal conductance with a predefined optimal stomatal conductance in a mathematical stomatal conductance model.

15. A method for the analysis of the stomatal conductance of a plant, comprising the steps of:

positioning a thermal imaging device, such that at least a portion of the plant is in an imaging region of the thermal imaging device, positioning a reference object, such that at least a portion of the reference surface of the reference object is located in the imaging region of the thermal imaging device, capturing, with the thermal imaging device, a thermal image of the plant and the reference surface in the imaging region, obtaining, with a thermal sensor of the reference object, a temperature sensor signal that is representative for a surface temperature of the reference surface, determining, with a processor device, the stomatal conductance of the plant, wherein the stomatal conductance is determined on the basis of the portion of the plant and the reference surface in the imaging region of the thermal imaging device shown in the captured thermal image, and compensating, with the processor device, the determined stomatal conductance of the plant, wherein the stomatal conductance is compensated on the basis of the portion of the plant and the reference surface in the imaging region of the thermal imaging device shown in the captured thermal image and the temperature sensor signal.

16. The method according to claim 15, further comprising the step of determining, with the processor device and on the basis of the stomatal conductance and micro climate data of an environment of the plant, one or more of:

a dew point status distribution of the plant, a maximum allowable air temperature decrease for which condensation on the plant is prevented, a maximum allowable increase in air humidity for which condensation on the plant is prevented, and a maximum allowable decrease in surface temperature of the plant for which condensation on the plant is prevented, wherein the micro climate data of the environment of the plant is at least temporarily stored on a memory of the processor device and comprises one or more of:

an air temperature of the environment, and a relative air humidity of the environment.

17. The method according to claim 15, further comprising the steps of:

transmitting the compensated stomatal conductance to a control unit of a lighting system, comparing, with the control unit, the compensated stomatal conductance with a predefined optimal stomatal conductance for the plants, and controlling, with the control unit, an illumination source of the lighting system on the basis of the comparison.

18. The method according to claim 17, wherein the controlling of the illumination source is the controlling of one or more of:

activation of the illumination source to emit light for illuminating the plants, deactivation of the illumination source to cancel illumination of the plants when a certain predefined illumination duration has lapsed, the intensity of the light that is emitted by the illumination source, and/or the spectrum of the light that is emitted by the illumination source.

19. The method according to claim 17, wherein the comparing by the control unit is done on the basis of a mathematical stomatal conductance model.

* * * * *